(12) United States Patent
Laghi et al.

(10) Patent No.: US 9,216,099 B2
(45) Date of Patent: Dec. 22, 2015

(54) METHOD AND APPARATUS OF AN INTEGRATED GEL SEALING LINER

(71) Applicants: Aldo A Laghi, Clearwater, FL (US);
Kevin McLoone, Dunedin, FL (US);
Neil Tagner, Boca Raton, FL (US)

(72) Inventors: Aldo A Laghi, Clearwater, FL (US);
Kevin McLoone, Dunedin, FL (US);
Neil Tagner, Boca Raton, FL (US)

( * ) Notice: Subject to any disclaimer, the term of this patent is extended or adjusted under 35 U.S.C. 154(b) by 117 days.

(21) Appl. No.: 14/279,709

(22) Filed: May 16, 2014

(65) Prior Publication Data

US 2014/0249650 A1     Sep. 4, 2014

Related U.S. Application Data

(63) Continuation-in-part of application No. 13/494,877, filed on Jun. 12, 2012, now Pat. No. 8,852,291.

(51) Int. Cl.
| | |
|---|---|
| *A61F 2/78* | (2006.01) |
| *D04B 1/22* | (2006.01) |
| *D04B 21/20* | (2006.01) |
| *D04B 35/36* | (2006.01) |
| *A61F 2/50* | (2006.01) |

(52) U.S. Cl.
CPC ............. *A61F 2/7812* (2013.01); *D04B 1/225* (2013.01); *D04B 21/205* (2013.01); *D04B 35/36* (2013.01); *A61F 2002/5053* (2013.01); *A61F 2002/5056* (2013.01); *A61F 2002/785* (2013.01); *A61F 2002/7818* (2013.01)

(58) Field of Classification Search
CPC ...................... A61F 2/7812; A61F 2002/7818
See application file for complete search history.

(56) References Cited

U.S. PATENT DOCUMENTS

| | | |
|---|---|---|
| 3,991,424 A | 11/1976 | Prahl |
| 6,508,842 B1 | 1/2003 | Caspers |
| 7,001,563 B2 | 2/2006 | Janusson et al. |
| 7,118,602 B2 | 10/2006 | Bjarnason |
| 7,363,778 B2 | 4/2008 | Pickering et al. |
| 7,895,863 B2 | 3/2011 | Smith et al. |
| 8,034,120 B2 | 10/2011 | Egilsson et al. |
| 8,372,159 B2 | 2/2013 | Mackenzie |

FOREIGN PATENT DOCUMENTS

CN          103353830 A          10/2013

*Primary Examiner* — David H Willse
(74) *Attorney, Agent, or Firm* — Henry J. Recla

(57) ABSTRACT

A gel liner made by starting initially with a one-piece knitted tubular sock-shaped fabric having a closed distal end section of gel impermeable knitted fabric and an open proximal end section of gel impermeable knitted fabric and being a gel permeable loosely knitted fabric. Molding the liner to have a gel cushion layer on its interior surface with the gel passing through and partially embedding the yarns of the proximal fabric section with the outermost portions of the yarns free of gel to form at least one annular seal whereby the proximal end section forming a seal not inhibited in deformation and/or elongation by the fabric when the liner is worn thereby reducing or eliminating any twisting or discomfort of the liner during ambulation caused by the annular seal.

64 Claims, 12 Drawing Sheets

METHOD AND APPARATUS OF AN INTEGRATED GEL SEALING LINER

This is a continuation-in-part application of U.S. application Ser. No. 13/494,877, filed on Jun. 12, 2012, now U.S. Pat. No. 8,852,291, issued on Oct. 7, 2014.

TECHNICAL FIELD

The present invention relates generally to method of making a suspension-type gel cushioned liner to be worn over an amputee's residual limb regardless of the amputation being a leg amputation below-the-knee, BTK, or above-the-knee, ATK, but could also relate to an arm amputation below-the-elbow, BTE, or above-the-elbow, ATE. The gel cushioned liner of the present invention is designed to create suction between the liner and a socket, which suction is enhanced by an annular seal designed to promote a more secure fit of the prosthesis to the residuum of the wearer while greatly reducing, if not eliminating, inhibited blood flow through the residuum caused by the annular seals and the associated manufacturing processes used to create them of current prior art liners rendering such liners uncomfortable.

BACKGROUND

Over the course of the last several decades, various methods of suspending prostheses to the residual limb of an amputee were invented. One in particular involved a docking means that included a distal attachment fabricated into the distal end of an elastomeric interface or liner which was rolled onto the residual limb. After the interface was rolled onto the limb, the distal attachment would engage a locking means built into the socket of the prosthesis thereby locking the prosthesis on the patient's limb. This system became a standard in the industry. Manufacturers began producing these interfaces or liners with a fabric layer on the outer surface of the interface to help increase both the durability and ease of insertion into the sockets.

Further advancements were found in suspending the prostheses to a residual limb by creating an airtight seal between the liner mounted on the residual limb of the patient and the socket of the prosthesis to hold the prosthesis on the limb by suction. In some prostheses, one-way expulsion valves were located proximate to the distal end of the socket to expel any remaining air between the liner and the socket and thus create a more effective suspension of the prosthesis. Other prostheses included an evacuation pumping system attached to the distal end of the socket to evacuate the interstitial area between the liner and socket. When the prosthesis is fitted tightly to the limb, the patient feels more secure and perceives the prosthesis to be lighter. A tightly fitted prosthesis gives the amputee the feeling that the prosthesis is more of an extension to the residual limb, not just an addition. In order to enhance the evacuation of air out of the interstitial area of the prostheses, the interface or liner was lined with a fabric on the outer surface thereof to act as a wicking device for the air to travel through and out of the socket. Historically, the liner would have fabric on the external portion of the liner, and these liners are often produced anywhere from 12 inches in length to 20 inches in length. If a below the knee amputee has a limb 6 inches long from the knee joint, the socket would extend the medial and lateral walls a little more proximal, and because of knee flexion the liner may extend another 2-8 inches above the knee. In order to create a seal with the suspension sleeve, the sleeve must extend beyond the liner an additional 2-3 inches to seal against the skin. The added bulk and additional length increase that are associated with this method of using a suspension sleeve to create this suction suspension are two major factors developers have sought for many years to overcome.

To further enhance and maintain the suction created in suspension liners, annular seals have been incorporated into the liners to act as an elastic band around the residuum of the amputee. One example of such a suspension liner is disclosed in U.S. Pat. No. 6,508,842 to Caspers, incorporated herein by reference. Caspers discloses a suspension liner. As best illustrated in FIG. 18, the suspension liner includes urethane liner 92 having an outer fabric cover 130 with an annular seal 140. As disclosed in col. 13, lines 60 and 61, the annular seal is made from the same material as layer 92. As disclosed in col. 14, lines 1-10, the annular seal 140 may be an extension of liner 92 passing through the fabric cover 130. The Caspers invention is typical of a vacuum pumping type suspension system wherein the annular seal 140 acts as an elastic band around the residuum of the amputee. Another example of this type of suspension liner is disclosed in U.S. Pat. No. 8,034,120 to Egilsson, et al. incorporated herein by reference. Egilsson, et al. disclose a suspension liner 310 as best illustrated in FIGS. 45-47 and disclosed in col. 11, line 44 through col. 14, line 26. As disclosed in column 12, lines 41-43, the embodiment of FIGS. 45-47 is similar to the embodiment of FIGS. 43 and 44. The liner includes two tubular textile sections, a first section 312 and second section 314, defining a continuous profile 324. The Klasson patent (U.S. Pat. No. 4,923,474) is referenced in the Egilsson, et al. patent at col. 5, lines 37-58 as a prior art example of how an outer textile cover is molded to an inner layer of silicone. The Klasson molding technique is applied in the manufacture of the embodiment shown in FIGS. 45-47. The textile sections 312 and 314 (which are comparable to textile sections 212 and 214 of FIGS. 43 and 44) are secured to each other along seam 326. As disclosed in col. 11, lines 49-51, the first material segment 212 of FIGS. 43 and 44 may have stiffness greater than the stiffness of the second material segment 214. This would imply that material segment 312 of FIG. 45 has a greater stiffness than material segment 314. As disclosed in col. 13, lines 44-55, during the molding process, silicone is squeezed through the first material section. As disclosed in col. 13, lines 56-62, the embodiment of FIG. 45 may include a single layer of silicone instead of the double layers 324 and 326 as shown in FIG. 47. Although material segment 312 has a greater stiffness than segment 314, does not necessarily mean that the number of stitches per centimeter is greater in segment 312. Just the opposite is shown. Egilsson et al. also recognize that the profile of the seals is not limited to arcuate or curvilinear, but may be substantially linear as disclosed in col. 12, lines 36-40.

Although the prior art inventions discussed above have benefited amputees by enhancing the suction effect of the liner to the limb of the amputee, they do have certain drawbacks. One major problem associated with such suspension liners is that the annular seals are restricted by the stiffness of the fabrics extending through the seals during the molding process. Such annular seals are limited in deformation and elongation due to the confining embedded fabric and therefore cause the seals to compress the residuum in the adjacent annular region. Horizontal seams stitched across the transverse axis of such prior art to hold different material sections together can also cause compression and discomfort in the residuum. Such prolonged compression actually squeezes the limb thereby inhibiting the flow of blood which leads to irritation not to mention other difficulties especially if the amputee is diabetic, hypertensive, arthritic, etc.

As discussed above, when the prosthesis is fitted tightly to the limb, the patient feels more secure and perceives the prosthesis to be lighter. A tightly fitted prosthesis gives the amputee a more comfortable feeling that the prosthesis is more of an extension to the residual limb, not just an addition. However, the addition of one or several annular seals or seams to the suspension liner inhibiting the flow of blood detracts from such a comfortable feeling especially during the course of a day where the residuum may swell and contract from everyday ambulation.

Maximum comfort is a critical component to the amputee (and consequentially, to their prosthetist) during their search for the correct prosthetic liner. Thus, there is still a need in the art for a prosthetic liner which overcomes the deficiencies of the prior art. As such, the present invention provides a solution to such problems as will be described hereafter.

BRIEF SUMMARY OF THE INVENTION

The method of making the gel liner of the present invention incorporates fabric on its outer surface except in a portion of at least one annular seal that is free of any fabric constrictions, at least, on its outer surface.

By stating that the at least one annular seal is free of any fabric constrictions on its outer surface is intended to mean that there may be fabric embedded or partially embedded within the annular seal. However, the section of fabric embedded or partially embedded within the annular seal is selected, as will be discussed hereinafter, to not inhibit deformation in the radial direction and/or elongation in the axial direction of the annular seal when donning or during normal ambulation of the wearer or during adjustment of the liner in response to discomfort of the liner during ambulation. In other words, by providing the annular seal free of any constricting fabric, as the liner is donned, the amputee will be able to stretch the seal portion of the liner to the extent necessary to allow the flow of blood through the residuum for the proper level of comfort. An important aspect of the present invention is that the annular seal portion is free to elongate in the axial direction as it is deformed in the radial direction. Thus, as the amputee ambulates during the course of a day, the unconstrained annular seal will be able to deform and elongate freely between the residuum and socket, thereby relieving any discomfort that would otherwise be caused by the prior art seals compressing the residuum too tightly inhibiting the flow of blood. Should the wearer experience discomfort due to inhibited blood flow, the liner could easily be adjusted lengthwise by stretching the seal to the extent necessary for maximum comfort without sacrificing the level of suction necessary for the above mentioned tight fit.

While the embodiments illustrated in the parent application included unconstrained annular seals wherein the fabric is either embedded in the gel layer or melted in the gel layer, the present invention also includes embodiments wherein the fabric layer is only partially embedded in the gel layer as will be explained hereinbelow. These embodiments also facilitate the insertion of the donned liner into a socket while maintaining an adequate seal with the socket interior during ambulation.

BRIEF DESCRIPTIONS OF THE DRAWINGS

FIGS. 9 and 9a are vertical sectional views of a sixth embodiment of the prosthetic liner of the present invention similar to the first embodiment except that the fabric of the intermediate section is partially embedded within the annular seal as illustrated in FIG. 9a.

FIG. 11 is a sectional view of the seventh embodiment of the prosthetic liner of the present invention with the fabric of the proximal section partially embedded within the annular seal as illustrated in FIG. 9a.

DETAILED DESCRIPTION OF THE INVENTION

Figure 1:
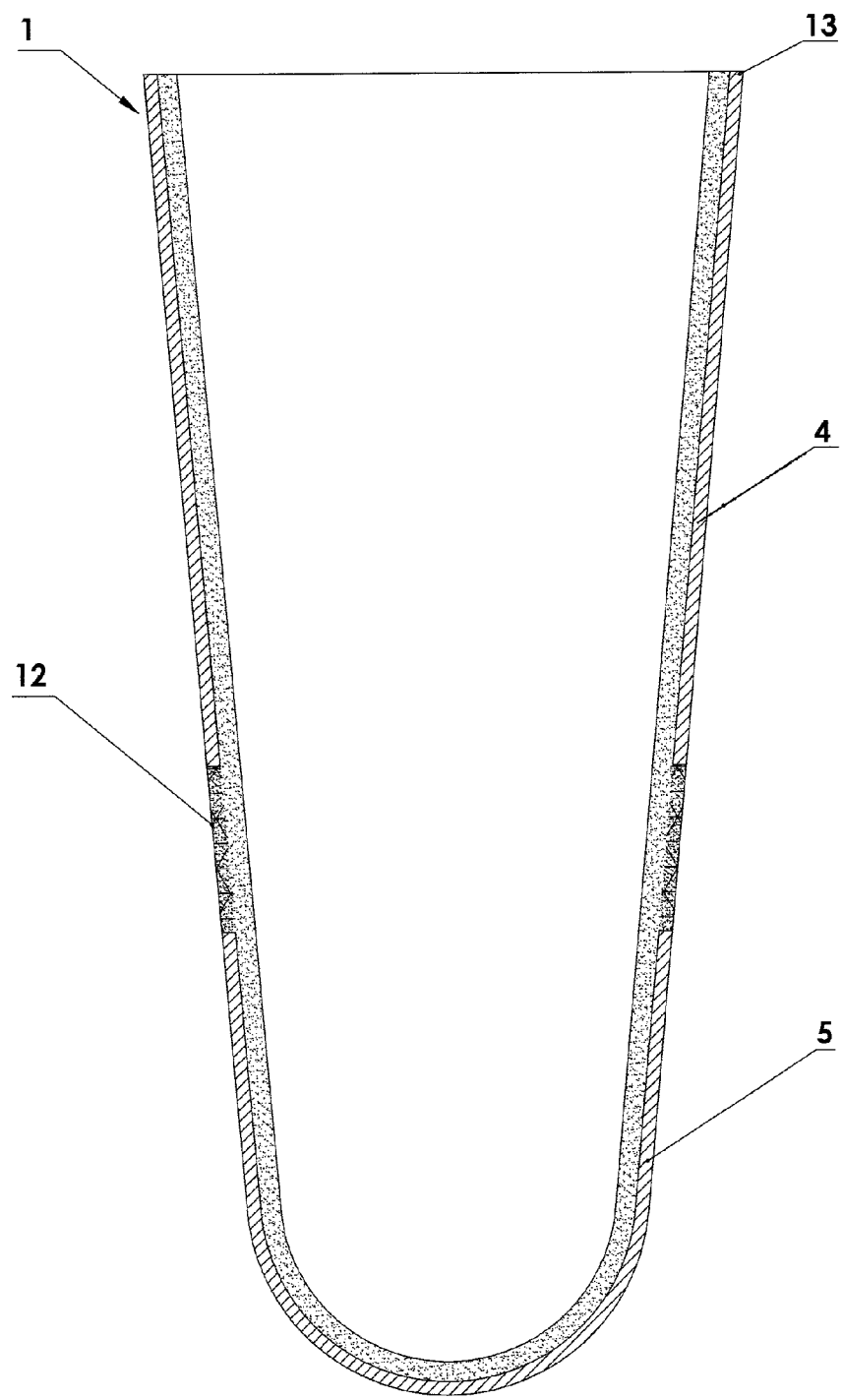
FIG. 1 is a vertical sectional view of a first embodiment of the prosthetic liner of the present invention with an intermediate annular seal located toward the distal end of the liner having fabric embedded within the annular seal.
Figure 2:
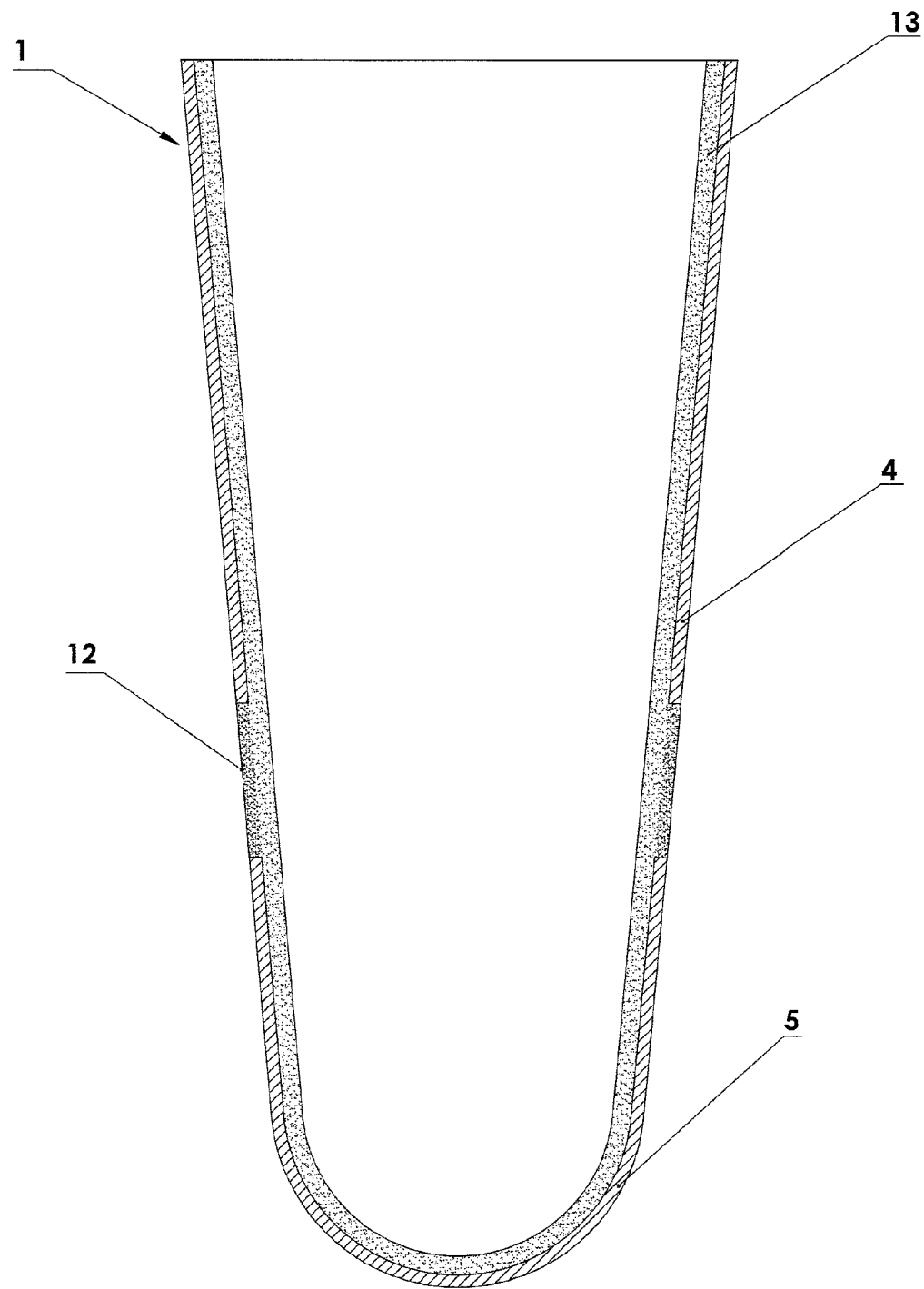
FIG. 2 is a vertical sectional view of a second embodiment of the prosthetic liner of the present invention with an intermediate annular seal located toward the distal end of the liner and being free of fabric within the annular seal.
Figure 3:
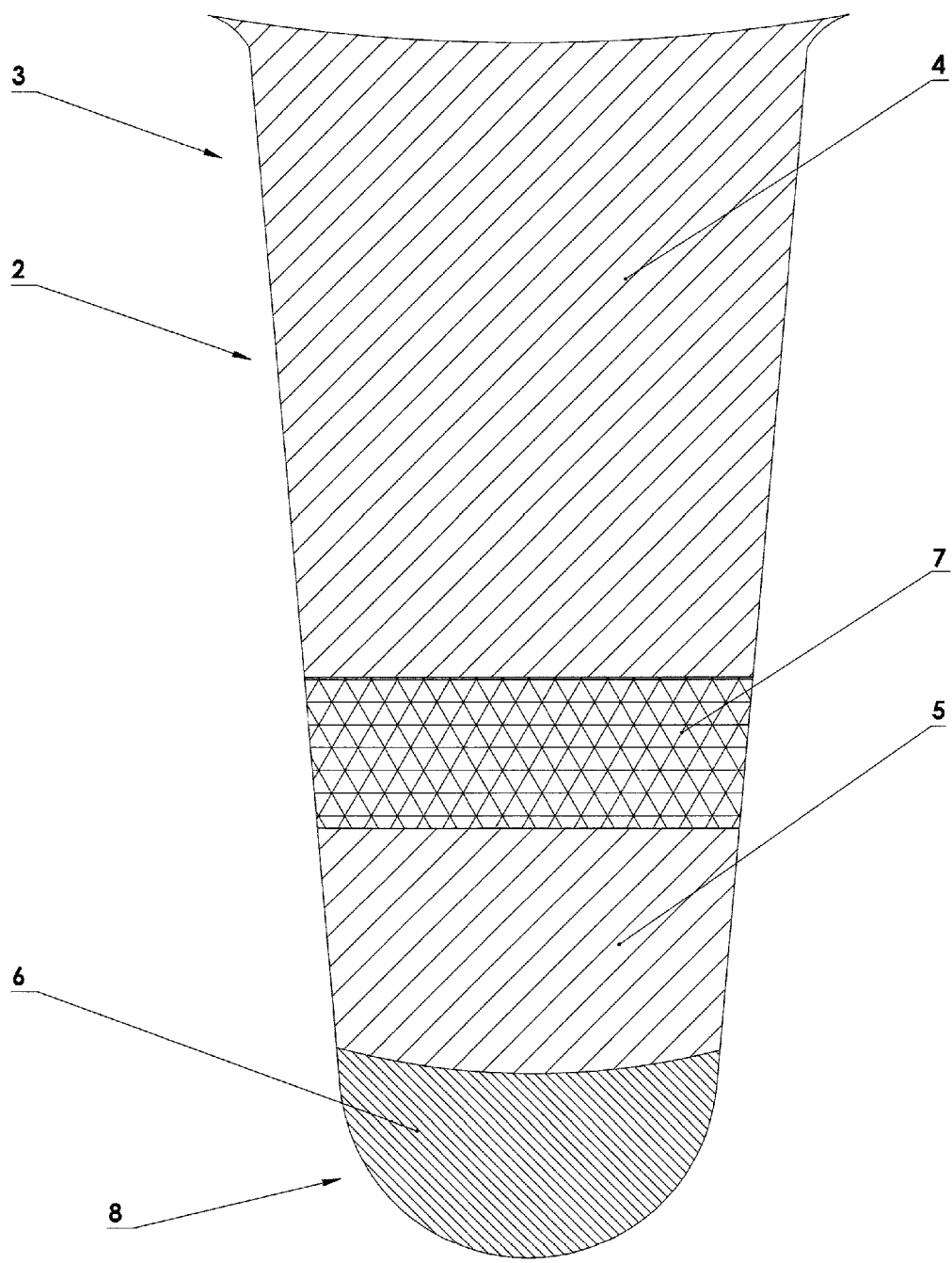
FIG. 3 is a perspective view of a one-piece tubular fabric layer having an intermediate section between distal and proximate sections initially used to manufacture the liners of the first or second embodiments of the present invention.
Figure 4:
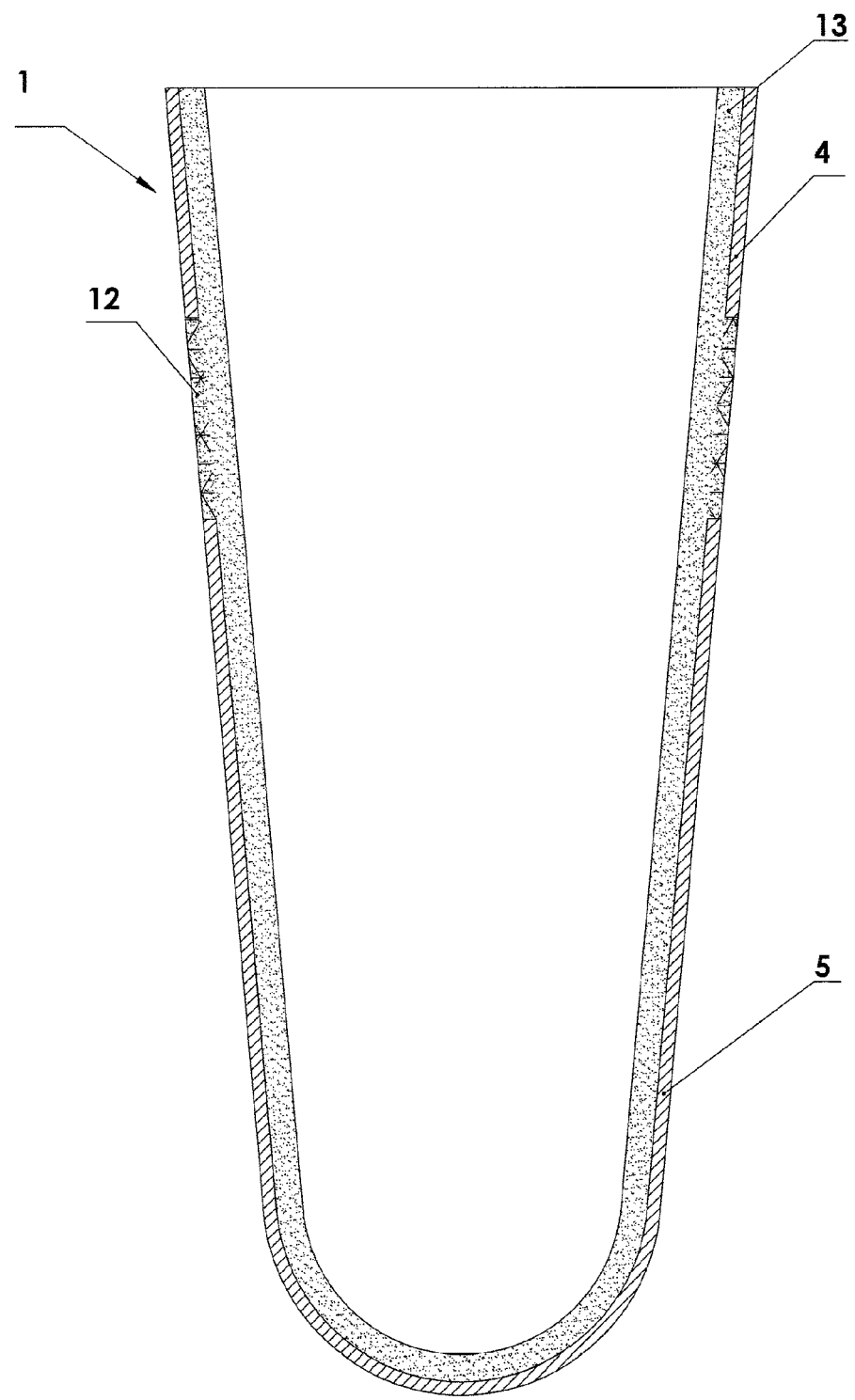
FIG. 4 is a vertical sectional view of a third embodiment of the prosthetic liner of the present invention with the annular seal located toward the proximal end of the liner.

Referring to FIGS. 1-4, first and second embodiments of the liner (1) of the present invention is made to initially include a one-piece tubular fabric "sock" structure (2) that includes a closed distal end section (8), an open proximal end section (3) and at least one intermediate section (7). As illustrated in FIG. 1, the finished liner (1) made by the molding process of the present invention is designed to have an outer tubular fabric (4) and (5) with annular seal (12) and gel interface (13) as an integral structure. The outer tubular fabric (4) and (5) is made as a one-piece tubular fabric as shown in FIG. 3. It can be made using a computerized flat-bed knitting machine or any other conventional knitting machinery of the type such as disclosed in U.S. Pat. No. 7,363,778 incorporated herein by reference. The flat-bed knitting style allows the one-piece tube to taper (grow) gradually from distal end to the proximal end and match the exact shape of the standard prosthetic liner. The computerized options allow the stitch cams to be tightened or loosened throughout any portion of the sock structure (1) depending on how much permeability is desired, and further allows different yarns or other materials such as nylon, meltable nylon, polyester, meltable polyester, meltable polyethylene, meltable polypropylene, Lycra, etc. to be introduced at any point in the knitting process. These type of knitting machines also allow the potential for knitting a much thicker, more tightly knitted fabric portion at any point in the sock and quickly transition to a very loose knit, more flaccid fabric portion or transition to any other desired knitted fabric portion. Referring to FIG. 3, the one-piece tubular fabric "sock" structure (2) of the present invention is made by programming the knitting machine to first knit a distal portion (5) preferably of a mixture of Coolmax® Polyester and stretchable synthetic elastane such as Lycra® selected so as not to permit gel to bleed through the fabric during the molding process as will be discussed hereinafter. The knitting machine may also be programmed to knit the distal portion (5) with an optional thicker portion (6) as illustrated in FIG. 3 having a thickness, for example, of (0.05"-0.50" or about 1.27 mm-12.7 mm) as an optional "reinforced" fabric distal area to reduce pistoning at the distal end of the liner and to allow the incorporation of a distal insert and locking pin thereto should it be desired to manufacture a combination locking liner/suction suspension system. The tubular fabric structure can be made to have roughly the same stretch characteristics as the traditional ALPS Beige Fabric liner, having Longitudinal Stretch of 5%-180%, and Transverse Stretch of 50%-250%. After making the distal portion (5) of the sock, the knitting machine can be programmed to knit the intermediate portion (7) which is embedded within the annular seal (12) by selecting a yarn and stitch per inch combination that is substantially less "stiff" than the distal portion (5) and proximal portion (4) so that the intermediate portion (7) will not substantially constrict the deformation of the annular seal in the radial direction or elongation of the annular seal in the longitudinal and transverse directions when the fibers remain embedded therein as illustrated in FIG. 1, or will not constrict the deformation of the annular seal in the radial direction or elongation of the annular seal in the longitudinal or transverse directions when the fibers are melted and blended within the annular seal as illustrated in FIG. 2. Preferably, the knitting machine is programmed to have the intermediate portion (7) be made of meltable fibers, such as meltable nylon fibers, meltable polyester fibers, meltable polyethylene, meltable polypropylene, etc. that will melt at a predetermined temperature, and with the stitch cams adjusted to have fewer stitches per inch whereby gel would flow freely through the intermediate portion (7). The meltable fibers will melt and blend with the gel should the temperature of the gel be selected above the melting temperature of the meltable fibers during the molding process as will be discussed hereinbelow. It must be pointed out that in order for this to occur, the meltable fiber is selected to have a melting temperature within the tolerable temperature limits of the gel itself. In other words, the melting temperature of the gel must be lower than the melting temperature of the fibers of the intermediate portion (7), but could withstand higher temperatures than the melting temperature of the fibers. However, the present invention will perform equally well if the temperature of the gel does not rise above the melting temperature of the fibers of the intermediate portion during the molding process if the fibers selected are of a less stiff (more flexible) yarn and seamlessly knitted in a loose stitch construction than the knit fabric in the upper or lower portions of the invention. The structural integrity of the fibers embedded therein may remain, as illustrated in FIG. 1, and will permit adequate movement of seal (12) when deformed between an amputee's stump and the inner surface of a socket but will not add additional constriction due to the combination of the less rigid yarn that is seamlessly knitted in a loose stitch construction to allow uninhibited blood flow. Following the intermediate portion, the knitting machine could be programmed again to seamlessly transition back into a portion similar to the knitting of the distal portion (5) to complete the sock.

Figure 5:
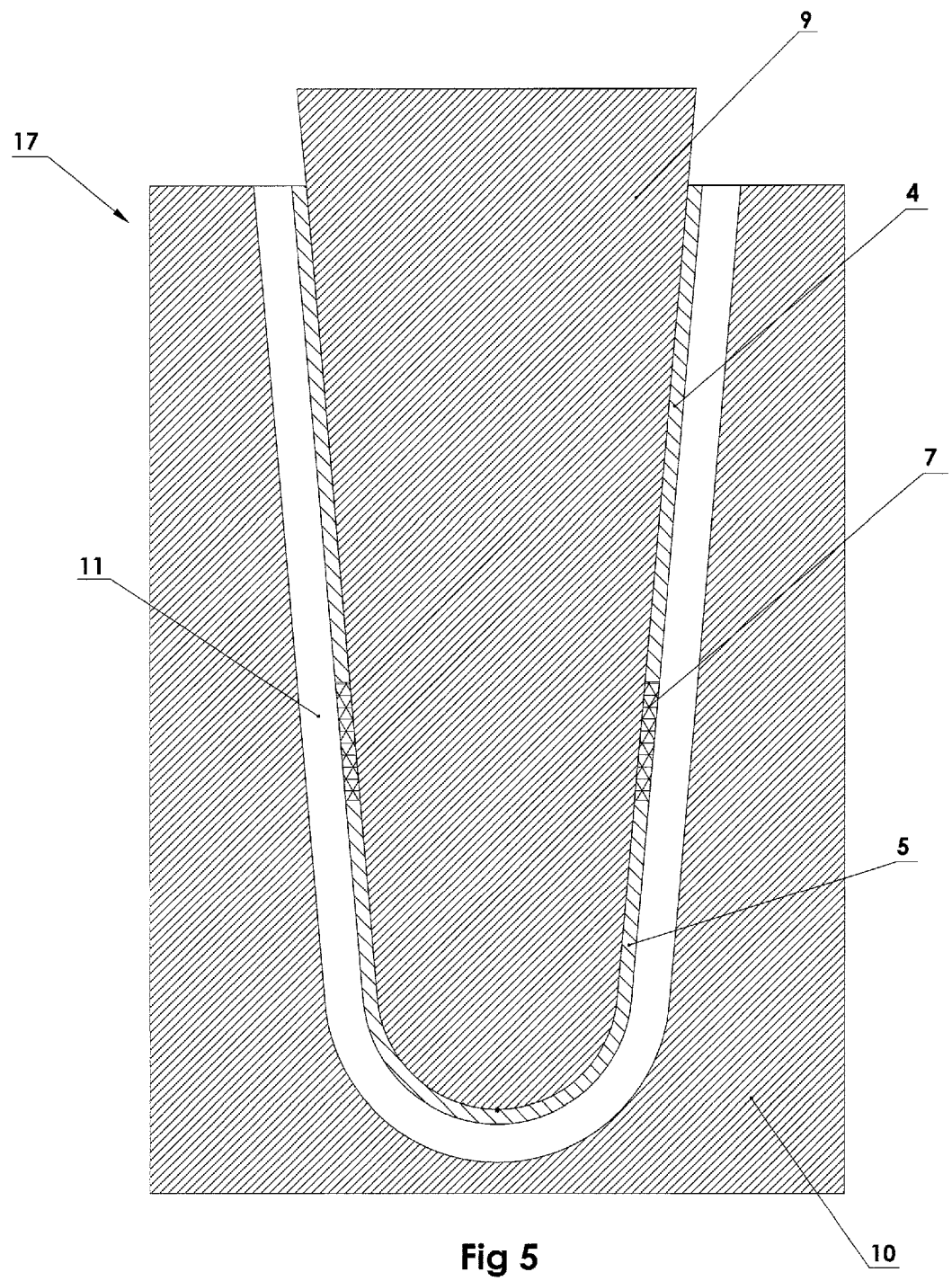
FIG. 5 is a sectional view of a male/female mold in which the prosthetic liner of the first, second and third embodiments of the present invention can be manufactured.

When the tubular sock is completed, the next step in the process is to install it into a molding machine (17) as illustrated in FIG. 5. These types of molding machines are conventional as for example, disclosed in U.S. Pat. No. 7,001,563 incorporated herein by reference. The molding machine includes a male core component (9) and a female component (10) and annular space (11) when the two components are mounted together. The knitted sock (2) is inverted prior to being mounted over the male component (9). The male component is then inserted into the female component and the system is sealed and ready for insertion of molten gel into space (11) between the two components. As the gel is inserted, it is adhered to the inner surface (now facing outward) of the fabric layer distal and proximal portions (4) and (5) without any bleed-through to the outer surface (now facing inward) of these portions. However, as the molten gel reaches the intermediate portion (7), it freely extrudes through the fabric interstices to the outer surface thereby encompassing the intermediate fabric portion. As discussed above, if the temperature at which the fibers of the intermediate fabric portion (7) melt is less than the temperature of the molten gel, the fibers will melt and blend with the gel. If the temperature at which the fibers of the intermediate fabric portion (7) melt is greater than the temperature of the molten gel, the fibers will be maintained and be embedded within the gel. Thus, after the intermediate fabric portion is engulfed with the molten gel, the fibers will either melt and blend with the molten gel, or be embedded therein, to form a substantially constriction-free seal (12). When the molded liner is cooled and removed from the molding machine, it is reverted to have the fabric covered portions facing outward. As shown in FIG. 1 or 2, the resulting seal (12) has an outer surface coextensive with the outer surfaces of the proximal and distal fabric portions (4) and (5). However, the outer surface of the seal (12) could extend slightly beyond the outer surface of fabrics (4) and (5) by modifying the male component (9) to have a slight recess to allow for a thicker seal. Furthermore, the location of the seal could be adjusted as, for example, illustrated in FIG. 4 closer to the proximal end of the liner by programming the knitting machine accordingly.

Figure 6:
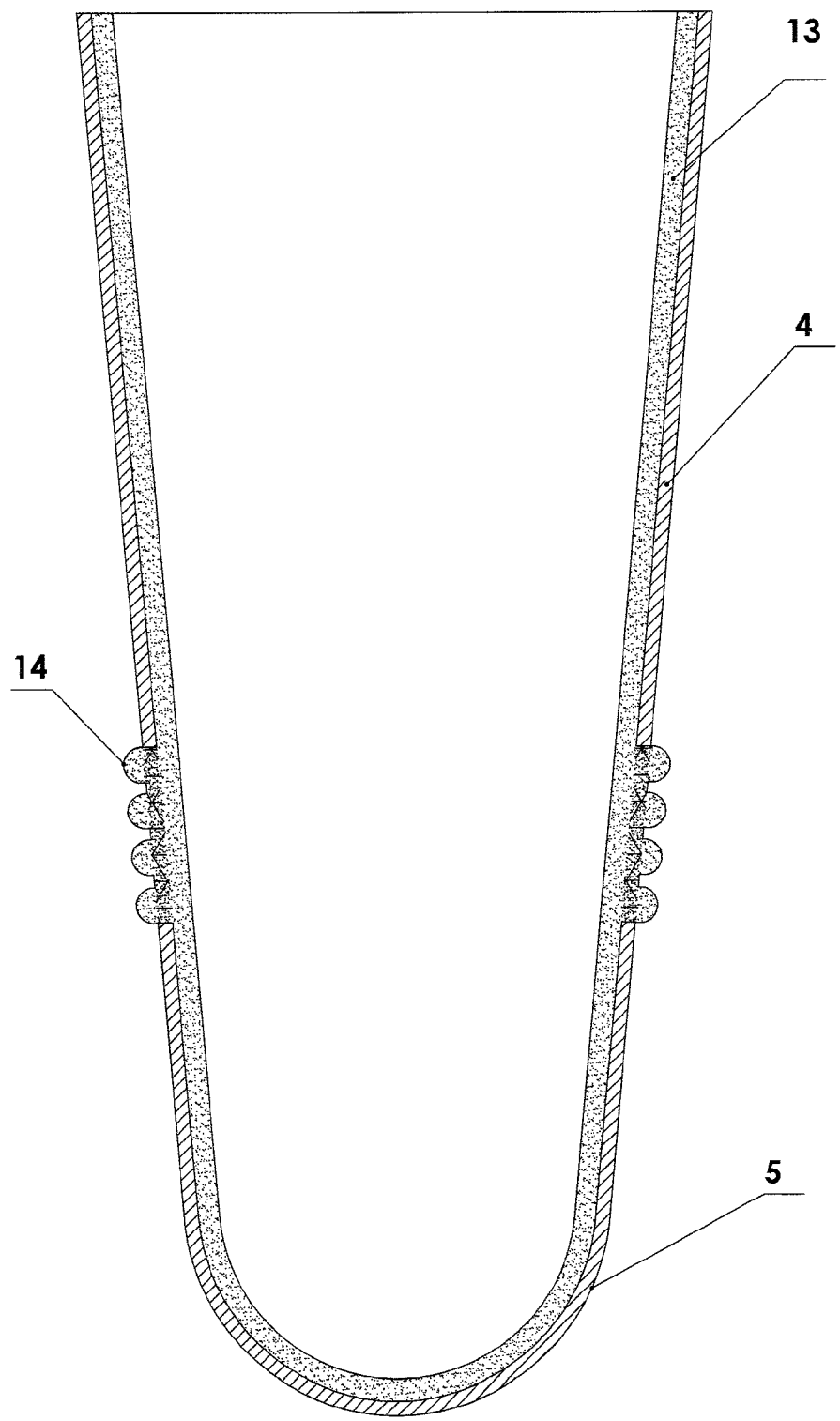
FIG. 6 is a vertical sectional view of a fourth embodiment of the prosthetic liner of the present invention with an alternative annular seal located toward the distal end of the liner.
Figure 7:
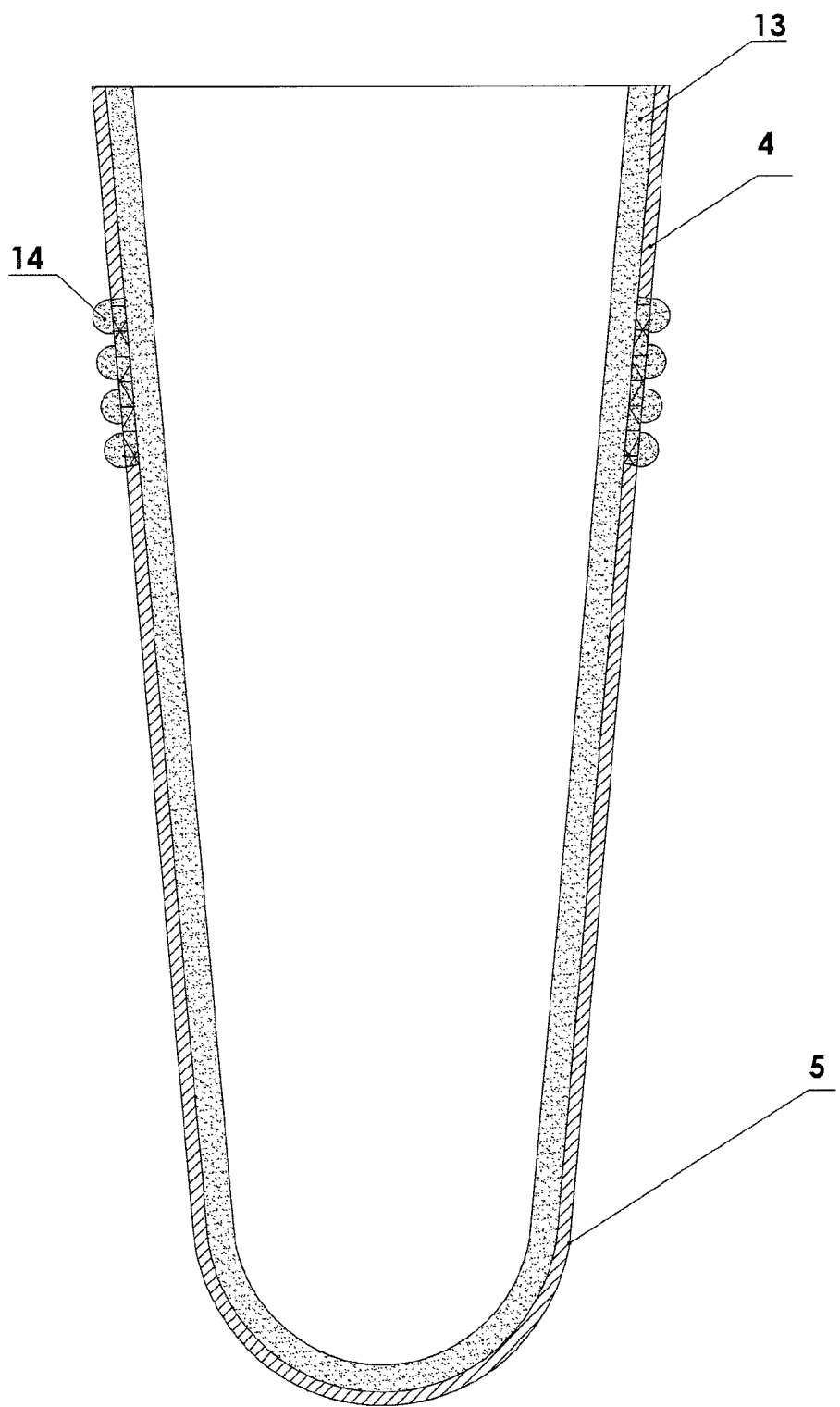
FIG. 7 is a vertical sectional view of a fifth embodiment of the prosthetic liner of the present invention with the alternative annular seal located toward the proximal end of the liner.
Figure 8:
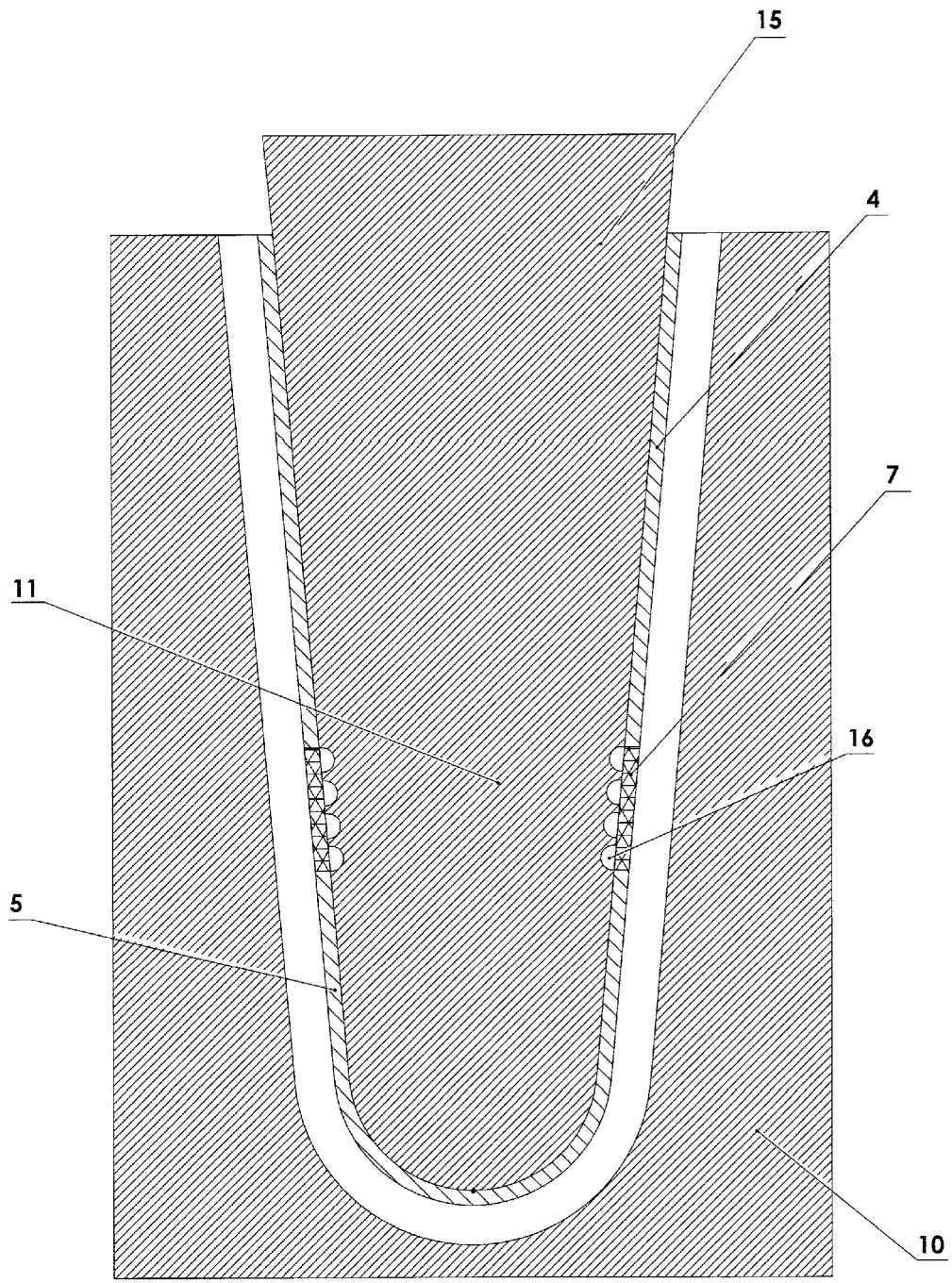
FIG. 8 is a sectional view of a male/female mold in which the fourth and fifth embodiments of the prosthetic liner with the alternative seal of the present invention can be manufactured.

Referring to FIGS. 6-8, fourth and fifth embodiments are illustrated similar to the first embodiment except that it has a raised bead shaped seal (14) formed by the modified male component (15) illustrated in FIG. 8. The male component includes recesses (16) which receive molten gel during the molding process which, when cooled, results in a constriction-free seal as shown in FIG. 6 or 7. The male component 15 could also be modified such that the seal (14) is located towards the proximal end of the liner as illustrated in FIG. 7.

Figure 9:
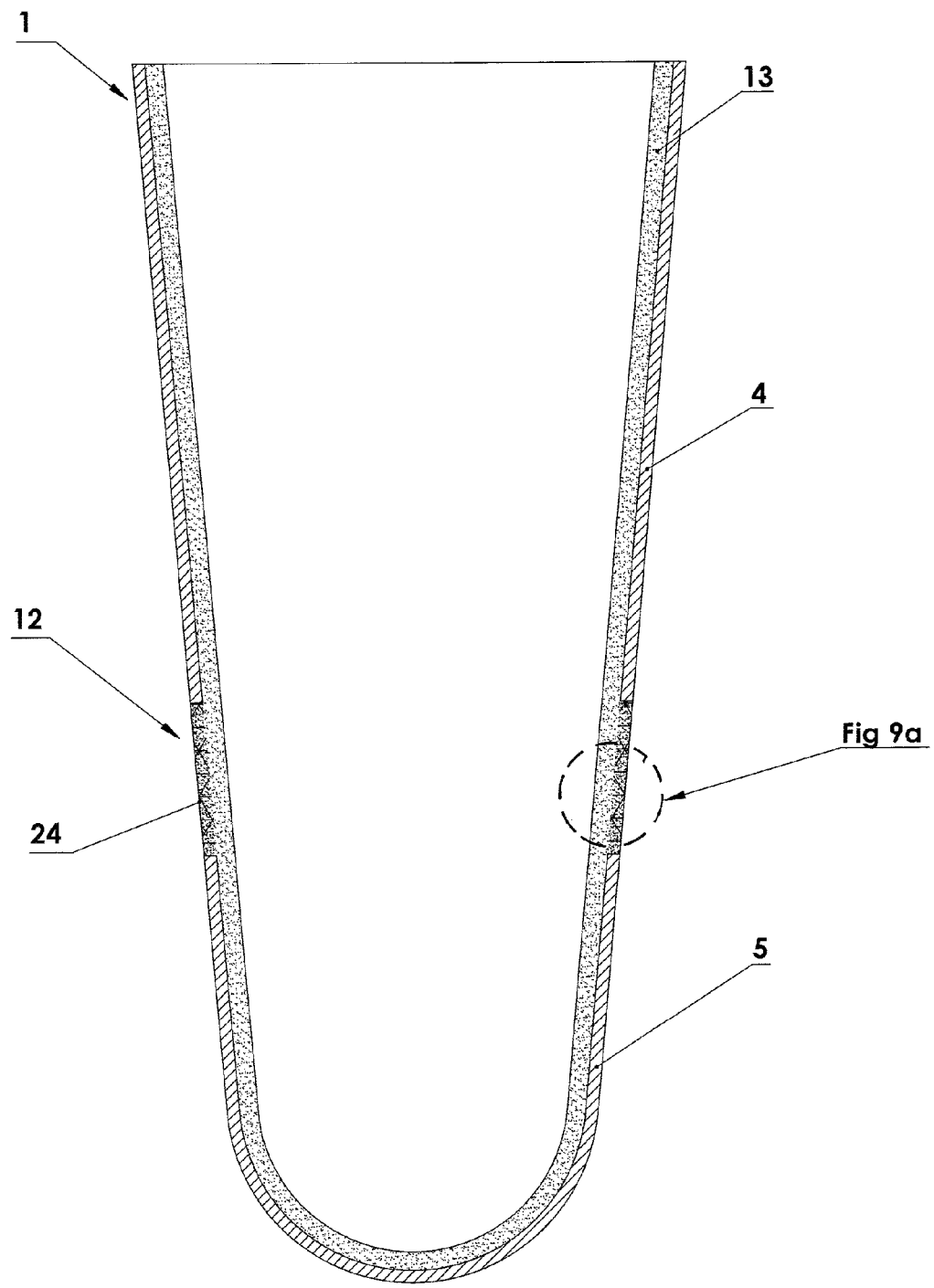
Figure 9A:
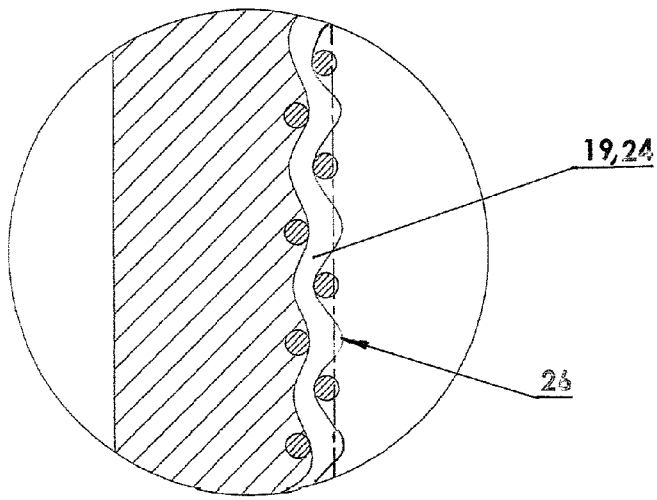

Referring to FIG. 9, a sixth embodiment is illustrated similar to the first embodiment of FIG. 1 except that the fabric (24) of the intermediate section (12) is only partially embedded in the annular seal as illustrated in FIG. 9a. The one-piece tubular fabric is knitted in the same manner as in the first embodiment with the exception that during the molding process, the threads of the fabric are coated only on the sides thereof that are not in contact with the male component of the molding machine. This is accomplished by controlling the flow, pressure and temperature of the inserted gel during the molding process such that the gel does not completely engulf the fabric threads but leaves the surface of the threads interfacing with the male component uncoated. Since the threads of the fabric are partially embedded in the gel layer, Applicants have found that this embodiment reduces the tackiness of the outer surface of the annular seal (12) which facilitates the insertion of the liner into a socket after being donned, but still provides a sufficient seal between the liner and socket.

Figure 10:
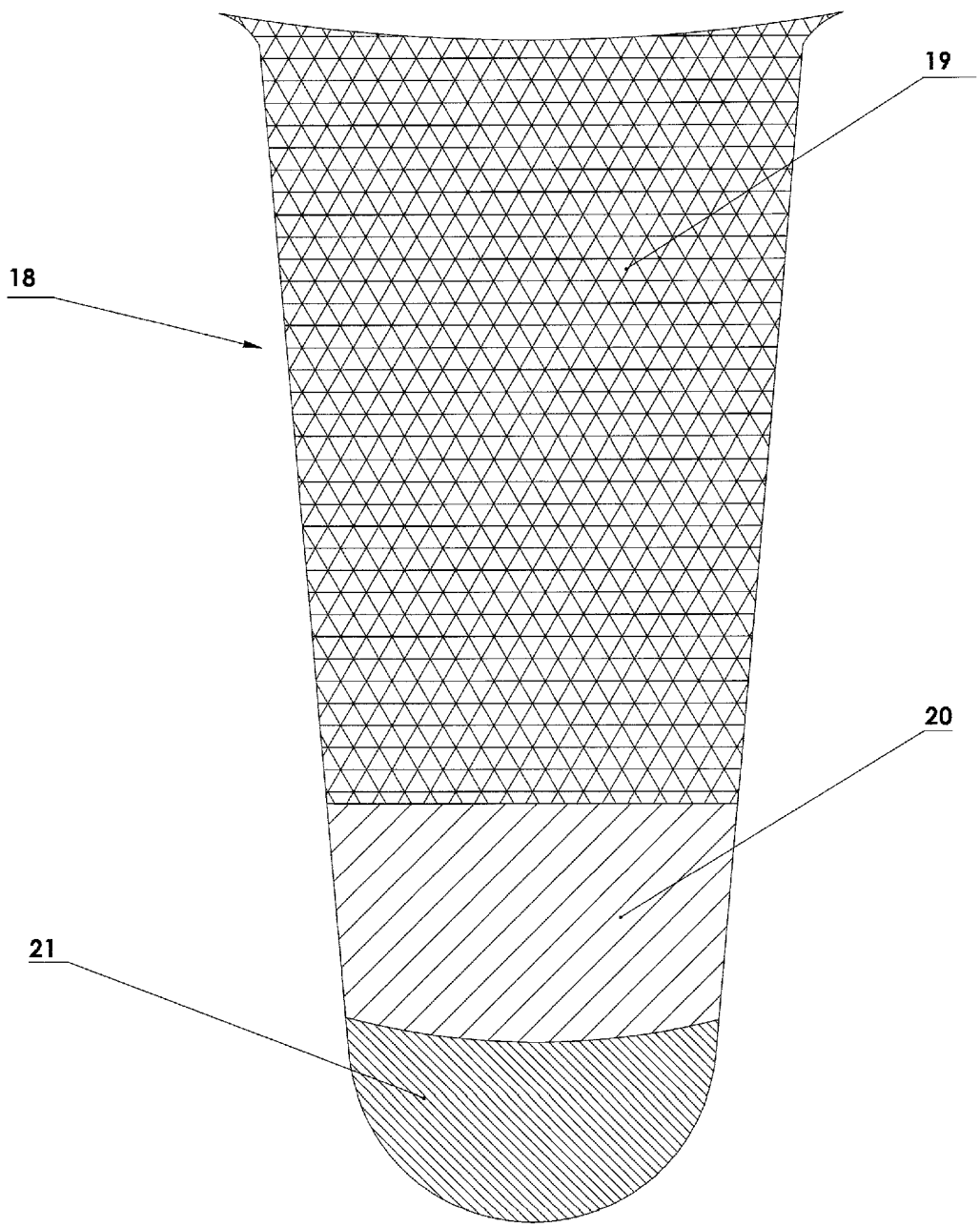
FIG. 10 is a perspective view of a one-piece tubular fabric layer of a seventh embodiment of the present invention having only proximal and distal sections and with an optional thickened distal end for a distal insert initially used to manufacture the liner of the present invention.
Figure 11:
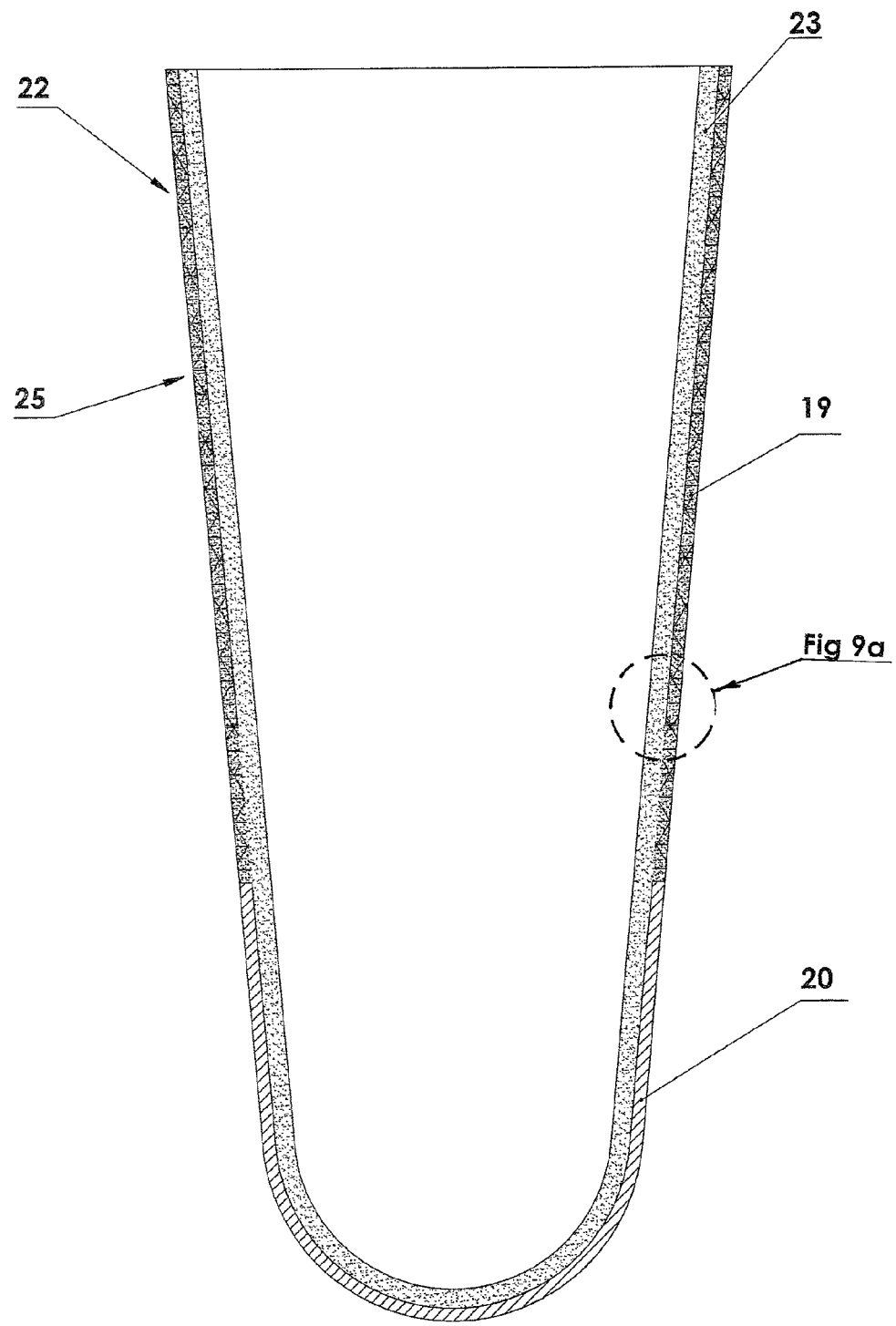

Referring to FIGS. 10 and 11, a seventh embodiment of the present invention (22) is illustrated having a one-piece tubular fabric (18). The one-piece tubular fabric (18) does not include an intermediate section. It includes a proximal section (19) and a distal section (20) which may have an optional thickened portion (21) should this embodiment have a distal insert attached thereto. In this embodiment, the entire proximal section (25) serves as an annular seal. The distal section (20) and optional distal end (21) are knitted in the same manner as the distal and optional sections (5) and (6) of the embodiment illustrated in FIG. 3. However, the entire proximal section (19) is knitted in the same manner as the intermediate section (7) of the first embodiment illustrated in FIG. 3 of the present invention, i.e., after making the distal portion (20) of the sock, the knitting machine can be programmed to knit the entire proximal portion (19) by selecting a yarn and stitch per inch combination that is substantially less "stiff" and will not constrict the deformation or elongation of the annular seal (25), when the fibers are partially embedded in the gel layer (23) as illustrated in FIG. 9a. Another advantage of this embodiment is that twisting of the donned liner within a socket is greatly reduced due to the extent of the annular seal (25).

The liner made by the process of the present invention provides an easy adjustable molding technique for manufacturing the liner because it starts with a one-piece liner. The gel interface of the preferred embodiment is covered with a tubular knit outer fabric layer except for the annular seal. The length of the annular seal of an intermediate section can be adjusted to approximately 0.5-3.0 inches and can be located anywhere along the length of the liner, or it can comprise the entire proximal section of the liner. Although not limited to any predetermined dimensions, the distal end can be adjusted to approximately 4-8 inches and the proximal section can be adjusted to approximately 10-14 inches. A great advantage of the process of the present invention is that the tubular fabric sock is initially knitted as a one-piece sock which, during the molding process, selectively may remain as a one-piece sock or become a two-piece fabric sock joined by the fabric-free annular seal simply by adjusting the temperature of the molten gel above or below the melting temperature of the fibers of the intermediate portion (7). This advantage saves manufacturing time by not having to knit separate multiple portions of the liner with different lengths, not having to secure multiple portions of the liner on the male component of the molding machine prior to injection, or not having to sew multiple portions of the liner together before mounting on the male component of the molding machine.

The liners of the present invention comprise a layer of elastomeric material (13 or 23) preferably of a type compatible with long periods of dynamic wearer contact. Such materials are known in the art and may include the following polymers, as well as gels which comprise them: silicones, polyurethanes; block copolymers such as styrene block copolymers, general non-limiting examples of which may include SEBS-, SEPS-, SEEPS-, SEEBS-, and other type styrene block copolymers. Further non-limiting examples of styrene block copolymers which may be useful in the liner of the present invention include so called "controlled distribution polymers," such as, for example, those disclosed in U.S. Pat. No. 7,226,484; United States Patent Application Publication No. 20070238835; and United States Patent Application Publication No. 20050008669. Other potentially useful polymers may include certain so-called "crystalline" polymers, such as, for example, polymers disclosed in U.S. Pat. Nos. 5,952,396; 6,420,475 and 6,148,830. The above list is non-limiting, and in general, the list of acceptable polymers and gels includes those known in the art to be useful for the fabrication of prosthetic liners. By the term "gel," is meant a polymer mixed with a plasticizer, such as mineral oil. An example of current liner using such gel is the "EZ Gel liner, available from Alps South L.L.C.

The unconstricted, low-profile seal designs of the present invention create a complete seal against the interior socket while permitting unconstricted deformation and elongation of the seal resulting in a more comfortable fit to a user. The fully knit fabric covering acts distally as a wick to draw any air inside the prosthesis to the outside of the closed system whether using a socket having a one-way valve in the distal end thereof, or a more elaborate suctioning system. The fabric covering of each embodiment acts both proximally and distally to facilitate ease of donning and doffing the liner.

As discussed above, the layer of cushioning material (13 or 23) could be a gel copolymer such as that sold by ALPS, silicone or polyurethane. The knitted tubular fabrics act to stabilize and cover the internal gel copolymer/silicone/polyurethane layer which exhibits stretch characteristics of 600%-2000% and a Modulus of 50-500 psi. against the residual limb. It is critical to note that in addition to the proprietary ALPS Gel noted above, many different inner materials could be used, including but not limited to: silicone, thermoplastic elastomers (triblock), copolymer Styrenic gels, and polyurethane gels. The fabrics utilized would likely demonstrate longitudinal stretch characteristics of 5% to 180%, and transverse stretch characteristics of 50% to 250%, and could be between 0.30 mm and 1.5 mm in thickness.

Figure 12A:
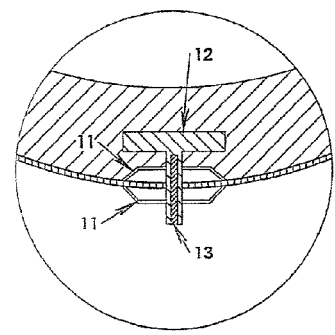
FIG. 12a is an enlarged cross-sectional view of a first embodiment of a distal insert that can be molded in the distal end of any of the liners of the present invention.
Figure 12:
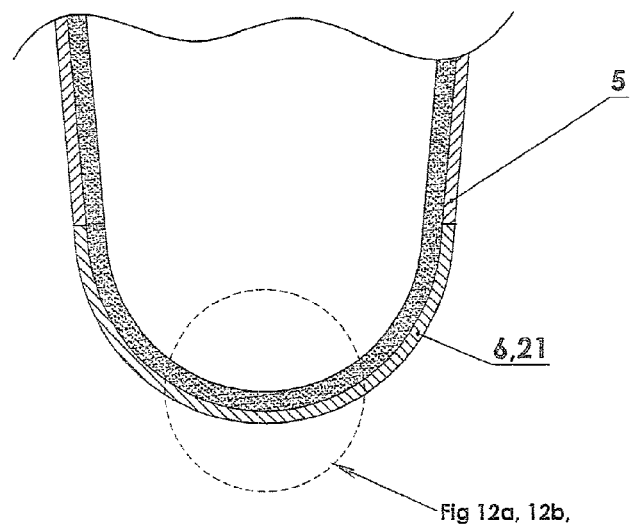
FIG. 12 is a partial sectional view of the distal end of the first through seventh embodiments depicting an encircled distal region in which a distal insert is attached.
Figure 12B:
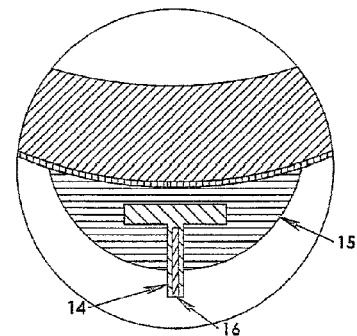
FIG. 12b is an enlarged cross-sectional view of a second embodiment of a distal insert that can be molded in the distal end of any of the liners of the present invention.

As illustrated in FIGS. 3, 10 and 12, the respective embodiments of the present invention can be modified to have thicker portion (6) or (21) such that the addition of a distal insert illustrated in FIGS. 12, 12a and 12b can be molded into or onto the distal end of the liner for attaching a locking pin thereto. While the distal inserts of FIGS. 12a and 12b are simply shown graphically, they are not intended as limiting the present invention, wherein any well known insert could be employed.

The foregoing relates to the preferred exemplary embodiments of the invention, it being understood that other variants and embodiments thereof are possible within the spirit and scope of the invention, the latter being defined by the appended claims.

What is claimed is:

1. A method of making a cushion liner for enclosing an amputation stump and sealing with an interior of a prosthetic socket comprising:
   knitting a one-piece elastic tubular-shaped fabric with a programmable knitting machine;
   said one-piece elastic tubular-shaped fabric having an open proximal end for introduction of said stump and a closed distal end opposite said open proximal end and with said fabric having an outer surface and an inner surface;
   programming said knitting machine to knit said one-piece elastic tubular-shaped fabric to have at least one intermediate section;

programming said knitting machine to knit said one-piece elastic tubular-shaped fabric, except for said at least one intermediate section, with first yarns and as a gel impermeable fabric;

programming said knitting machine to knit said at least one intermediate section with second yarns in a loose stitch construction and as a gel permeable fabric, said second yarns being less rigid than said first yarns;

inverting said knitted one-piece elastic tubular-shaped fabric to have said inner surface facing outward;

mounting said inverted one-piece elastic tubular-shaped fabric on a male component of a gel molding system;

inserting molten gel into an annular space between said male component and a female component of said gel molding system such that said gel adheres to the inner surface of said one-piece elastic tubular-shaped fabric that is gel impermeable and protrudes through and engulfs the second yarns of said one-piece elastic tubular-shaped fabric of said intermediate section on all surfaces except for the surfaces of said second yarns in direct contact with the male component of the molding machine;

allowing said cushion liner to cool thereby forming said molten gel into an elastic cushioning gel layer;

removing said cushion liner from said molding system after said cushion liner has cooled;

reverting said cushion liner such that said outer surface faces outwardly thereby having said cushion liner covered with said gel impermeable fabric except for said at least one intermediate section and said outer surface of said at least one intermediate section having said gel permeable fabric partially embedded in said cushioning gel layer thereby defining an annular seal less constricted to elongation in the transverse and longitudinal directions and deformation in the radial direction than the remaining sections of said cushion liner, whereby said annular seal will be free to expand and contract without inhibiting blood flow and causing discomfort to an amputee's stump within a prosthetic socket.

2. A method of making a cushion liner as claimed in claim 1, wherein said fabric of said one-piece elastic tubular-shaped fabric comprises polyester, rayon, nylon, polyethylene, polypropylene, or any combination thereof.

3. A method of making a cushion liner as claimed in claim 1, wherein said fabric of said one-piece elastic tubular-shaped fabric comprises a mixture of polyester and elastane fibers.

4. A method of making a cushion liner as claimed in claim 1, wherein said gel comprises a polymer mixed with a plasticizer.

5. A method of making a cushion liner as claimed in claim 2, wherein said gel comprises a polymer mixed with a plasticizer.

6. A method of making a cushion liner as claimed in claim 3, wherein said gel comprises a polymer mixed with a plasticizer.

7. A method of making a cushion liner as claimed in claim 4, wherein said polymer is selected from the group consisting of silicone, thermoplastic triblock copolymers, styrene block copolymers, and polyurethane.

8. A method of making a cushion liner as claimed in claim 5, wherein said polymer is selected from the group consisting of silicone, thermoplastic triblock copolymers, styrene block copolymers, and polyurethane.

9. A method of making a cushion liner as claimed in claim 6, wherein said polymer is selected from the group consisting of silicone, thermoplastic triblock copolymers, styrene block copolymers, and polyurethane.

10. A method of making a cushion liner as claimed in claim 1, wherein said one-piece elastic tubular-shaped fabric is knitted to have a thickness of between 0.30 mm and 1.5 mm.

11. A method of making a cushion liner as claimed in claim 10, wherein said knitting machine is programmed to knit said one-piece elastic tubular-shaped fabric at a distal-most portion of said closed distal end with a thickness in the range of 0.05 to 0.5 inches, thereby adapting said distal-most portion to have a distal insert attached thereto.

12. A method of making a cushion liner as claimed in claim 11, wherein said distal-most portion includes a distal insert molded into said gel.

13. A method of making a cushion liner as claimed in claim 11, wherein said distal-most portion includes a distal insert attached to said fabric of said distal-most portion.

14. A method of making a cushion liner as claimed in claim 11, further programming said knitting machine such that said at least one intermediate section has an axial length of from 0.5 to 3.0 inches.

15. A method of making a cushion liner as claimed in claim 12, further programming said knitting machine such that said at least one intermediate section has an axial length of from 0.5 to 3.0 inches.

16. A method of making a cushion liner as claimed in claim 13, further programming said knitting machine such that said at least one intermediate section has an axial length of from 0.5 to 3.0 inches.

17. A method of making a cushion liner as claimed in claim 1, further comprising molding said cushion liner such that outer surfaces of said second yarns of said gel permeable fabric defining said annular seal are co-extensive with said outer surfaces of said first yarns of said gel impermeable fabric of said one-piece elastic tubular-shaped fabric.

18. A method of making a cushion liner as claimed in claim 1, further comprising molding said at least one tubular-shaped intermediate section to be disposed toward said distal end.

19. A method of making a cushion liner as claimed in claim 1, further comprising molding said at least one tubular-shaped intermediate section to be disposed toward said proximal end.

20. A method of making a cushion liner as claimed in claim 1, wherein said one-piece elastic tubular-shaped fabric, except for said at least one intermediate section, is knitted to have 5%-180% longitudinal stretch characteristics and 50%-250% transverse stretch characteristics.

21. A method of making a cushion liner as claimed in claim 1, wherein said elastomeric cushioning gel layer has stretch characteristics of 600%-2000% and a Modulus of 50-500 psi.

22. A cushion liner for enclosing an amputation stump and sealing with an interior of a prosthetic socket, said cushion liner comprising:

an open tubular-shaped proximal end and a closed tubular-shaped distal end and at least one tubular-shaped intermediate section, each of said open tubular-shaped proximal end, said closed tubular-shaped distal end and said at least one tubular-shaped intermediate section comprised of an elastomeric cushioning gel layer having an inner surface that substantially conforms to the shape of said amputation stump and an outer surface;

a one-piece knitted elastic tubular-shaped fabric having an inner surface and an outer surface, said inner surface adhered to said outer surface of said elastomeric cushioning gel layer, except for said at least one tubular-shaped intermediate section;

said one-piece knitted elastic tubular-shaped fabric comprised of first yarns and being gel impermeable, except in said at least one tubular-shaped intermediate section;
said one-piece knitted elastic tubular-shaped fabric in said at least one tubular-shaped intermediate section comprised of second yarns and being gel permeable;
said second yarns partially embedded in said elastomeric cushioning gel layer in said at least one tubular-shaped intermediate section, said second yarns being less rigid than said first yarns and being of a loose stitch construction, said second yarns having their outermost surfaces free of gel and their remaining surfaces embedded in said elastomeric cushioning gel layer;
said outer surface of said one-piece knitted elastic tubular-shaped fabric in said at least one tubular-shaped intermediate section defining an annular seal less constricted to elongation in the transverse and longitudinal directions and deformation in the radial direction than the remaining sections of said cushion liner for sealing with a prosthetic socket, whereby said annular seal will be free to expand and contract without inhibiting blood flow and causing discomfort to an amputee's stump within a prosthetic socket.

23. A cushion liner as claimed in claim 22, wherein said second yarns of said at least one tubular-shaped intermediate section defining said annular seal have outer surfaces co-extensive with said outer surfaces of said first yarns of said one-piece knitted gel impermeable elastic fabric of said cushion liner.

24. A cushion liner as claimed in claim 22, wherein said at least one tubular-shaped intermediate section is disposed toward said closed tubular-shaped distal end.

25. A cushion liner as claimed in claim 22, wherein said at least one tubular-shaped intermediate section is disposed toward said open tubular-shaped proximal end.

26. A cushion liner as claimed in claim 22, wherein said one-piece knitted gel impermeable elastic fabric is comprised of polyester, rayon, nylon, polyethylene, polypropylene, or any combination thereof.

27. A cushion liner as claimed in claim 22, wherein said one-piece knitted gel impermeable elastic fabric is comprised of a mixture of polyester and elastane fibers.

28. A cushion liner as claimed in claim 22, wherein said elastomeric cushioning gel layer comprises a polymer mixed with a plasticizer.

29. A cushion liner as claimed in claim 28, wherein said polymer is selected from the group consisting of silicone, thermoplastic triblock copolymers, styrene block copolymers, and polyurethane.

30. A cushion liner as claimed in claim 22, wherein said one-piece knitted gel impermeable elastic fabric has a thickness of between 0.30 mm and 1.5 mm.

31. A cushion liner as claimed in claim 22, wherein said one-piece knitted gel impermeable elastic fabric has a distal-most portion of said closed tubular-shaped distal end with a thickness in the range of 0.05 to 0.5 inches, thereby adapting said distal-most portion to have a distal insert attached thereto.

32. A cushion liner as claimed in claim 31, wherein said distal-most portion includes a distal insert molded into said elastomeric cushioning gel layer.

33. A cushion liner as claimed in claim 31, wherein said distal-most portion includes a distal insert attached to said one-piece knitted gel impermeable elastic fabric of said distal-most portion.

34. A cushion liner as claimed in claim 22, wherein said at least one tubular-shaped intermediate section has an axial length of from 0.5 to 3.0 inches.

35. A cushion liner as claimed in claim 22, wherein said elastomeric cushioning gel layer having stretch characteristics of 600%-2000% and a Modulus of 50-500 psi.

36. A cushion liner as claimed in claim 22, wherein said one-piece knitted elastic tubular-shaped fabric, except for said at least one tubular-shaped intermediate section, has 5%-180% longitudinal stretch characteristics and 50%-250% transverse stretch characteristics.

37. A method of making a cushion liner for enclosing an amputation stump and sealing with an interior of a prosthetic socket comprising:
knitting a one-piece elastic tubular-shaped fabric with a programmable knitting machine;
said one-piece elastic tubular-shaped fabric having an open proximal end for introduction of said stump and a closed distal end opposite said open proximal end and with said fabric having an outer surface and an inner surface;
programming said knitting machine to knit said one-piece elastic tubular-shaped fabric to have a distal section followed by a proximal section;
programming said knitting machine to knit said distal section with first yarns and as a gel impermeable fabric;
programming said knitting machine to knit said proximal section with second yarns in a loose stitch construction and as a gel permeable fabric, said second yarns being less rigid than said first yarns;
inverting said knitted one-piece elastic tubular-shaped fabric to have said inner surface facing outward;
mounting said inverted one-piece elastic tubular-shaped fabric on a male component of a gel molding system;
inserting molten gel into an annular space between said male component and a female component of said gel molding system such that said gel adheres to the inner surface of said one-piece elastic tubular-shaped fabric that is gel impermeable in said distal section and protrudes through and engulfs the second yarns of said one-piece elastic tubular-shaped fabric that is gel permeable in said proximal section on all surfaces of said second yarns except for the surfaces of said second yarns in direct contact with the male component of the molding machine;
allowing said cushion liner to cool thereby forming said molten gel into a cushioning gel layer;
removing said cushion liner from said molding system after said cushion liner has cooled;
reverting said cushion liner such that said outer surface of said one-piece elastic tubular-shaped fabric faces outwardly thereby having said distal section of said cushion liner covered with said gel impermeable fabric and said proximal section having said gel permeable fabric partially embedded in said cushioning gel layer thereby defining an annular seal less constricted to elongation in the transverse and longitudinal directions and deformation in the radial direction than the distal section of said cushion liner, whereby said annular seal will be free to expand and contract without inhibiting blood flow and causing discomfort to an amputee's stump within a prosthetic socket.

38. A method of making a cushion liner as claimed in claim 37, wherein said fabric of said one-piece elastic tubular-shaped fabric comprises polyester, rayon, nylon, polyethylene, polypropylene, or any combination thereof.

39. A method of making a cushion liner as claimed in claim 37, wherein said fabric of said one-piece elastic tubular-shaped fabric comprises a mixture of polyester and elastane fibers.

40. A method of making a cushion liner as claimed in claim 37, wherein said gel comprises a polymer mixed with a plasticizer.

41. A method of making a cushion liner as claimed in claim 38, wherein said gel comprises a polymer mixed with a plasticizer.

42. A method of making a cushion liner as claimed in claim 39, wherein said gel comprises a polymer mixed with a plasticizer.

43. A method of making a cushion liner as claimed in claim 40, wherein said polymer is selected from the group consisting of silicone, thermoplastic triblock copolymers, styrene block copolymers, and polyurethane.

44. A method of making a cushion liner as claimed in claim 41, wherein said polymer is selected from the group consisting of silicone, thermoplastic triblock copolymers, styrene block copolymers, and polyurethane.

45. A method of making a cushion liner as claimed in claim 42, wherein said polymer is selected from the group consisting of silicone, thermoplastic triblock copolymers, styrene block copolymers, and polyurethane.

46. A method of making a cushion liner as claimed in claim 37, wherein said one-piece elastic tubular-shaped fabric is knitted to have a thickness of between 0.30 mm and 1.5 mm.

47. A method of making a cushion liner as claimed in claim 37, wherein said knitting machine is programmed to knit said one-piece elastic tubular-shaped fabric at a distal-most portion of said closed distal end with a thickness in the range of 0.05 to 0.5 inches, thereby adapting said distal-most portion to have a distal insert attached thereto.

48. A method of making a cushion liner as claimed in claim 47, wherein said distal-most portion includes a distal insert molded into said gel.

49. A method of making a cushion liner as claimed in claim 47, wherein said distal-most portion includes a distal insert attached to said fabric of said distal-most portion.

50. A method of making a cushion liner as claimed in claim 37, further comprising molding said cushion liner such that outer surfaces of said second yarns of said gel permeable fabric defining said annular seal are co-extensive with said outer surfaces of said first yarns of said gel impermeable fabric of said one-piece elastic tubular-shaped fabric.

51. A method of making a cushion liner as claimed in claim 37, wherein said one-piece elastic tubular-shaped fabric, except for said proximal section, is knitted to have 5%-180% longitudinal stretch characteristics and 50%-250% transverse stretch characteristics.

52. A method of making a cushion liner as claimed in claim 37, wherein said elastomeric cushioning gel layer has stretch characteristics of 600%-2000% and a Modulus of 50-500 psi.

53. A cushion liner for enclosing an amputation stump and sealing with an interior of a prosthetic socket, said liner comprising:

an open tubular-shaped proximal section terminating in a proximal end and a closed tubular-shaped distal section terminating in a distal end, each of said open tubular-shaped proximal section and said closed tubular-shaped distal section comprised of an elastomeric cushioning gel layer having an inner surface that substantially conforms to the shape of said amputation stump and an outer surface;

a one-piece knitted elastic tubular-shaped fabric having an inner surface and an outer surface, said inner surface of said one-piece knitted elastic tubular-shaped fabric adhered to said outer surface of said closed tubular-shaped distal section of said elastomeric cushioning gel layer;

said one-piece knitted elastic tubular-shaped fabric adhered to said closed tubular-shaped distal section comprised of first yarns and being gel impermeable in said closed tubular-shaped distal section;

said one-piece knitted elastic tubular-shaped fabric in said open tubular-shaped proximal section comprised of second yarns and being gel permeable in said open tubular-shaped proximal section;

said second yarns of said one-piece knitted elastic tubular-shaped fabric partially embedded in said elastomeric cushioning gel layer in said open tubular-shaped proximal section, said second yarns being less rigid than said first yarns and being of a loose stitch construction, said second yarns having their outermost surfaces free of gel and their remaining surfaces embedded in said open tubular-shaped proximal section of said elastomeric cushioning gel layer;

said open tubular-shaped proximal section outer surface defining an annular seal less constricted to elongation in the transverse and longitudinal directions and deformation in the radial direction than the distal section of said cushion liner for sealing with a prosthetic socket, whereby said annular seal will be free to expand and contract without inhibiting blood flow and causing discomfort to an amputee's stump within a prosthetic socket.

54. A cushion liner as claimed in claim 53, wherein said second yarns of said one-piece knitted elastic tubular-shaped fabric of said open tubular-shaped proximal section defining said annular seal have outer surfaces co-extensive with said outer surfaces of said first yarns of said one-piece knitted gel impermeable elastic fabric of said closed tubular-shaped distal section of said cushion liner.

55. A cushion liner as claimed in claim 53, wherein said one-piece knitted gel impermeable elastic fabric is comprised of polyester, rayon, nylon, polyethylene, polypropylene, or any combination thereof.

56. A cushion liner as claimed in claim 53, wherein said one-piece knitted gel impermeable elastic fabric is comprised of a mixture of polyester and elastane fibers.

57. A cushion liner as claimed in claim 53, wherein said elastomeric cushioning gel layer comprises a polymer mixed with a plasticizer.

58. A cushion liner as claimed in claim 57, wherein said polymer is selected from the group consisting of silicone, thermoplastic triblock copolymers, styrene block copolymers, and polyurethane.

59. A cushion liner as claimed in claim 53, wherein said one-piece knitted gel impermeable elastic tubular-shaped fabric has a thickness of between 0.30 mm and 1.5 mm.

60. A cushion liner as claimed in claim 53, wherein said one-piece knitted gel impermeable elastic fabric has a distal-most portion of said closed tubular-shaped distal section with a thickness in the range of 0.05 to 0.5 inches, thereby adapting said distal-most portion to have a distal insert attached thereto.

61. A cushion liner as claimed in claim 60, wherein said distal-most portion includes a distal insert molded into said elastomeric cushioning gel layer.

62. A cushion liner as claimed in claim 60, wherein said distal-most portion includes a distal insert attached to said one-piece knitted gel impermeable elastic fabric of said distal-most portion.

63. A cushion liner as claimed in claim 53, wherein said elastomeric cushioning gel layer having stretch characteristics of 600%-2000% and a Modulus of 50-500 psi.

64. A cushion liner as claimed in claim 53, wherein said one-piece knitted gel impermeable elastic fabric of said closed tubular-shaped distal section, has 5%-180% longitudinal stretch characteristics and 50%-250% transverse stretch characteristics.

* * * * *